US012667460B2

(12) United States Patent
Parthasarathy et al.

(10) Patent No.:  US 12,667,460 B2
(45) Date of Patent:       Jun. 30, 2026

(54) SCAFFOLD STRUCTURES AND COMPOSITIONS FACILITATING OSSEOINTEGRATION

(71) Applicants: ATLAS SCIENCE AND TECHNOLOGY, LLC, Niskayuna, NY (US); DUCLOS SCIENTIFIC, LLC, Weybridge, VT (US)

(72) Inventors: Gautam Parthasarathy, Niskayuna, NY (US); Daniel J. Erno, Clifton Park, NY (US); Chitresh Bhushan, Schenectady, NY (US); Cathleen Ann Hoel, Schenectady, NY (US); Sara Kelly Peterson, Schenectady, NY (US); Jessica Susanne Martinez, Niskayuna, NY (US); Brian Michael Davis, Niskayuna, NY (US); Steven Jude Duclos, Clifton Park, NY (US); Fiona Ginty, Saratoga Springs, NY (US)

(73) Assignees: DUCLOS SCIENTIFIC, LLC, Weybridge, VT (US); ATLAS SCIENCE AND TECHNOLOGY, LLC, Niskayuna, NY (US)

( * ) Notice: Subject to any disclaimer, the term of this patent is extended or adjusted under 35 U.S.C. 154(b) by 948 days.

(21) Appl. No.: 17/877,486

(22) Filed: Jul. 29, 2022

(65) Prior Publication Data
US 2024/0033092 A1      Feb. 1, 2024

(51) Int. Cl.
*A61F 2/30*          (2006.01)

(52) U.S. Cl.
CPC . *A61F 2/30771* (2013.01); *A61F 2002/30112* (2013.01); *A61F 2002/3093* (2013.01); *A61F 2002/30968* (2013.01); *A61F 2310/00011* (2013.01); *A61F 2310/00179* (2013.01); *A61F 2310/00329* (2013.01)

(58) Field of Classification Search
None
See application file for complete search history.

(56) References Cited

U.S. PATENT DOCUMENTS

| | | | |
|---|---|---|---|
| 10,155,069 | B2 | 12/2018 | Abdalla et al. |
| 10,265,155 | B2 | 4/2019 | Lu et al. |
| 10,943,701 | B2 | 3/2021 | Cole, Jr. et al. |
| 2014/0091491 | A1 | 4/2014 | Hung et al. |

(Continued)

FOREIGN PATENT DOCUMENTS

WO      WO-2011057318 A1 *   5/2011   ............. G06T 17/20

OTHER PUBLICATIONS

Koenderink J. et al. "Surface shape and curvature scales" 1992 Image Vision Comput 10(8):557-564 (Year: 1992).*

(Continued)

*Primary Examiner* — Javier G Blanco
(74) *Attorney, Agent, or Firm* — HESLIN ROTHENBERG FARLEY & MESITI P.C.

(57) ABSTRACT
The present discussion relates to the design fabrication and use of synthetic scaffold structure for bone growth. In certain implementations the scaffold structures are comprised of a plurality of repeating structures each defined by a local topology. The local topologies are defined at a subset of points in their respective volumes by various parameters including, but not limited to, shape index, curvedness, mean curvature, and Gauss curvature.

15 Claims, 15 Drawing Sheets

(56) References Cited

U.S. PATENT DOCUMENTS

| | | |
|---|---|---|
| 2015/0328004 A1* | 11/2015 | Mafhouz ............. A61F 2/30942 |
| | | 700/98 |
| 2019/0008923 A1 | 1/2019 | Kaplan et al. |
| 2021/0001014 A1 | 1/2021 | MacEwan |

OTHER PUBLICATIONS

Entezari et al., Architectural Design of 3D Printed Scaffolds Controls the Volume and Functionality of Newly Formed Bone, Advanced Healthcare Materials, vol. 8, Issue 1, 2019, 39 pages. https://onlinelibrary.wiley.com/doi/abs/10.1002/adhm.201801353.

Kao et al., Poly(dopamine) Coating of 3D Printed Poly(lactic acid) Scaffolds for Bone Tissue Engineering, Materials Science and Engineering: C, vol. 56, Issue 1, 2015, 165-173. https://doi.org/10.1016/j.msec.2015.06.028.

* cited by examiner

HA, n=20, surf:3px

Shape_index, chisq: P<2e-56; KS test: P=0.0e0;

HA, n=20, surf:3px

Curvedness, chisq; P<2e-25; KS test; P=0.0e0;

HA, n=20, surf:3px

Mean_Curvature, chisq: P<8e-60; KS test:
P=0.0e0;

HA, n=20, surf:3px

Gauss_Curvature, chisq: P<2e-54; KS test:
P=0.0e0;

Bone growth distribution [surf:1px]

All (N=49)          Additive (N=43)          BioOss (N=6)
(8.12 ± 4.17)          (8.01 ± 4.23)          (8.88 ± 3.98)

FIG. 16

SCAFFOLD STRUCTURES AND COMPOSITIONS FACILITATING OSSEOINTEGRATION

BACKGROUND

The subject matter disclosed herein relates to the design and manufacture of scaffold structures suitable for osseointegration.

Clinical management of bone defects is a significant and growing health problem. From trauma in the military domains to complications caused by cancer, arthritis, orthopedic and neurological issues in the civilian domains, there is an increased urgency towards solving unmet needs in bone defect management. Limb trauma and spinal cord injuries continue to be an important area or treatment for healthcare systems world-wide. While titanium implants and prosthetic devices have made significant progress in such contexts, they may be associated with complications such as due to their weight and lack of full osseointegration. Further, such implants and devices may contribute to osteoarthritis and osteoporosis and can in many instances lead to systemic discomfort.

With respect to the spine, the elimination of motion between vertebral segments is often a key technical challenge in spine repair. In many cases, bone grafts are used to promote fusion between vertebrae. The graft helps the vertebrae physically join to become solid bone and must work in concert with internal fixation measures to provide a structurally sound platform for bone growth. However, even though the use of bone substitutes and grafts for small scale defective regions has seen some development, there has been virtually no clinically significant development in the implementation of bone substitutes to address management of large-scale defects.

BRIEF DESCRIPTION

The disclosed embodiments are not intended to limit the scope of the claimed subject matter, but rather these embodiments are intended only to provide a brief summary of possible embodiments. Indeed, the disclosure may encompass a variety of forms that may be similar to or different from the embodiments set forth below.

In one embodiment, a scaffold structure is provided for facilitating bone growth. In accordance with aspects of this embodiment, the scaffold structure comprises a scaffold volume comprising a plurality of repeating structures defined by surface area and local topology. At least 2.5% of the surface area comprises local topologies with a shape index between –0.45 and 0.84 and a curvedness between 1.4 and 13.5.

In another embodiment, a scaffold structure is provided for facilitating bone growth. In accordance with aspects of this embodiment, the scaffold structure comprises a scaffold volume comprising a plurality of repeating structures defined by surface area and local topology. At least 2.5% of the surface area comprises local topologies with a mean curvature between –7.5 and 5 and a Gauss curvature between –60 and 20.

In a further embodiment, a scaffold structure is provided for facilitating bone growth. In accordance with aspects of this embodiment, the scaffold structure comprises a scaffold volume comprising a plurality of repeating structures defined by surface area and local topology. The local topologies are characterized by a subset of points in their respective surface having a shape index value and a curvedness value present within region 1 as set forth in FIG. 14 herein. The subset of point comprises 2.5% or more of the points of the respective surface.

In an additional embodiment, scaffold structure is provided for facilitating bone growth. In accordance with aspects of this embodiment, the scaffold structure comprises a scaffold volume comprising a plurality of repeating structures defined by surface area and local topology. The local topologies are characterized by a subset of points in their respective surface having a mean curvature value and a Gauss curvature value present within region 1 as set forth in FIG. 15 herein. The subset of point comprises 2.5% or more of the points of the respective surface.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 16 depicts box plots of bone volume percentage for additively manufactured scaffold structures, a control, and the combined results;

DETAILED DESCRIPTION

Figure 1:
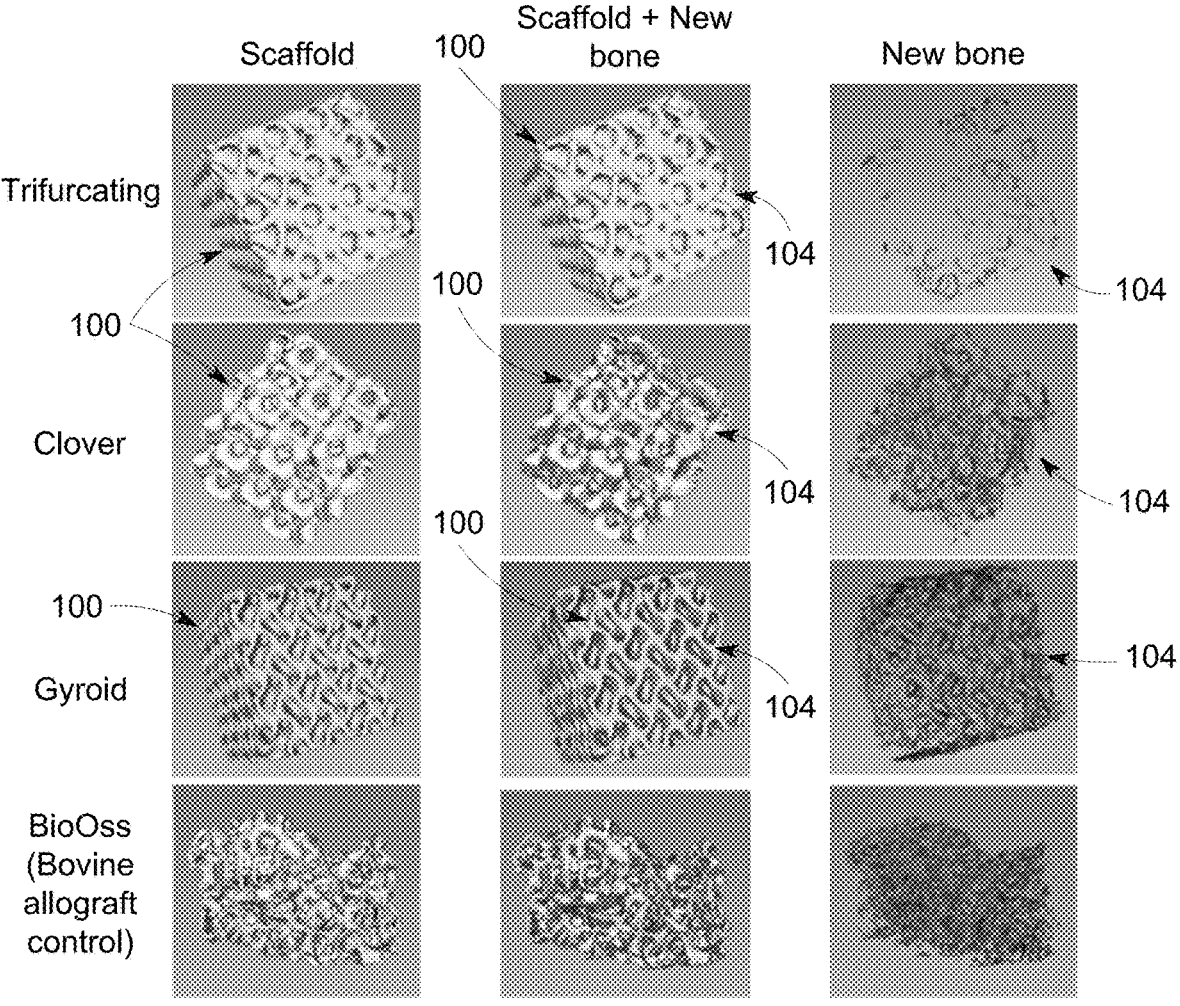
FIG. 1 depicts varying topologies of scaffold structures, in conjunction with a control, and the corresponding bone growth, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with biology-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example," "for instance," "such as," "e.g.," "including," "in certain embodiments," "in some embodiments," and "in one (an) embodiment."

As discussed herein, bone defect management is an area of ongoing development in various clinical contexts. By way of example, limb trauma and spinal cord injuries continue to be an important area or treatment for healthcare systems world-wide. In conventional approaches, titanium implants and prosthetic devices are often employed and have been refined over the years. However, such devices, even after refinement, still may be unsuited for certain patients or procedures due to their weight and lack of full osseointegration. Further, such implants and prosthetic devices may contribute to osteoarthritis and osteoporosis and can thereby lead to systemic in some instances.

Further, with respect to the spine, the elimination of motion between vertebral segments is a desirable outcome in spine repair. In many cases, bone grafts are used to promote fusion between vertebrae to help eliminate such motion, thereby achieving vertebrae stability and nerve decompression. The graft helps the vertebrae physically join to become solid bone and must work in concert with internal fixation measures to provide a structurally sound platform for bone growth. However, even though the use of bone substitutes and grafts for small-scale defective regions has seen some development, there has been virtually no clinically significant development in the implementation of bone substitutes to address management of large-scale defects.

With this in mind, approaches discussed herein are directed to actively managing bone defects, including large bone defects, and to facilitate repair of spine and musculo-skeletal injuries using manufactured living bone materials. In particular, the design, manufacture and use of scaffolds having topologies and compositions selected to stimulate and regulate growth of healthy bone is described. As discussed herein, such scaffold structures may be designed in accordance with triply periodic minimal surface (TPMS) principles, defined mathematically as infinite and periodic surface curvatures.

Fabrication systems and techniques to guide cell differentiation into mature bone tissue may be scalable as discussed herein. In accordance with the presently described approaches, implantable bone structures may be fabricated that may be used in implantation procedures to provide enhanced structural integrity along with sustained in vivo vascularization and bone formation, thereby enabling long-term assimilation of the bone substitute.

In certain implementations the living bone tissue and accompanying vascularization may be grown on or into scaffold structures. By way of example, such scaffold structures as described herein may be additively manufactured, such as using 3D-printing techniques, and may be composed of ceramics or other biocompatible materials that are compatible with additive manufacturing. By way of example, in one embodiment the scaffold structures may be additively synthesized by sintering a green ceramic body. In certain implementations the materials may include, but are not limited to including biologically compatible ceramic materials, such as materials in the calcium phosphate (CaP) class of materials (e.g., hydroxyapatite (HA) ceramic or a tricalcium phosphate (TCP)) as well as biologically compatible ceramic materials such as calcium sulfates, CaP cements, biphasic CaP, beta TCP, silicon nitride, aluminum oxide, zirconium oxide, bioactive glasses, carbon-silicon, and so forth. In certain implementations the materials may include biologically compatible metals or metal alloys such as, but not limited to, titanium or titanium alloys (e.g., Ti-6AL-4U), cobalt chrome, stainless steel, and so forth. Similarly, in other implementations the materials may include biologically compatible polymeric materials, such as, but not limited to polycaprolactone (PCL), polyether ether ketone (PEEK), poly(methyl methacrylate) (PMMA), polylactic acid (PLA), polytetrafluoroethylene, or polyurethane. As discussed herein, the use of additive manufacturing approaches, such as 3D-printing enables the development of load-bearing scaffolds with geometries optimized or otherwise selected for vascularization and bone formation.

Such scaffold structures may be fabricated to be patient-specific or, in other implementations, in a standardized form or shape (e.g., an out-of-the-box form or shape) that can be cut or otherwise modified for use with a given patient. By way of example, acquired image data (e.g., X-ray based image data, magnetic resonance image data, ultrasound image data, and so forth) may be used to non-invasively characterize the internal patient anatomy at the site the scaffold is to be deployed. The overall size and shape (e.g., external bulk geometry) of the scaffold structure may then be cut or modified for optimal interfacing to the existing anatomy of the patient.

In certain embodiments a scaffold structure may also be coated with biologics to improve one or more characteristics of the scaffold structure or the patient response when in use. By way of example, a scaffold structure may be coated or impregnated with a suitable biological material to improve patient acceptance or response, to minimize healing time, and/or to promote bone tissue growth and vascularization.

Further, as described herein the scaffold structures may be fabricated to include repeating open structures (e.g., cavities) and solid components having surface topologies (e.g., local surface topologies) that facilitate the growth of bone tissue on and in the scaffold structure. As used herein, a "cavity" may be understood to be a local feature including or associated with an open volume at the scale of the local topology. Each scaffold can be described by a global topology, which summarizes the geometry of the scaffold geometry. Each global topology is made up of a multitude of local topologies, which describe the point-by-point topology on the surface of the solid ceramic. By way of example, such surfaces may be characterized as being composed of features having local shape characteristics, such as a shape index and/or a measure of curvedness. In certain implementations the cavities and their corresponding surface features are not randomly distributed or positioned, but instead are distributed in a regular or repeating pattern.

The features comprising at each point on the cavity surfaces may be characterized by the principal curvatures ($k_1$ and $k_2$) and the normal vector at that point. The principal curvatures are signed scalar numbers that measure the maximum and minimum bending of a regular surface at each point (planar points have 0 curvature measure). The normal vector at a point on the surface is a unit vector that is perpendicular to the surface and points outward with respect of the scaffold surface. Principal curvature measures are positive when the regular surface bends in direction of the normal vector and negative otherwise. Other feature descriptors can be defined based on the principal curvatures, which include mean curvature $(MC)=((k_1+k_2))/2$, and Gaussian curvature $(GC)=(k_1 \cdot k_2)$. With respect to the terminology related to shape index and curvature, these concepts are also defined herein as represented in two-dimensional space described by the principal curvatures $k_1$ and $k_2$. With respect to shape index, this parameter may be mathematically defined as:

$$s = \frac{2}{\pi}\arctan\frac{k_2 + k_1}{k_2 - k_1} \quad k_1 \geq k_2 \tag{1}$$

Curvedness, as used herein, may be mathematically defined as:

$$R = \sqrt{\frac{k_1^2 + k_2^2}{2}}. \tag{2}$$

As discussed herein, bone formation on a scaffold structure is a function of material composition of the scaffold structure and of geometric and shape characteristics (e.g., topology) of the scaffold internal structure, including characteristic and properties of local or small-scale features (e.g., the respective local topology) associated with the cavity surfaces of the scaffold. The presently described scaffold structures, such as 3D-printed biocompatible ceramic scaffolds, may be used in place of non-load bearing void fillers that are currently in use.

In terms of evaluating the efficacy of the presently described scaffold structures for facilitating bone growth and vascularization, certain imaging approaches are described. In particular, certain evaluations or assessments are described in the context of bone growth quantification using μ-computed tomography (μCT). In the present context such μCT imagery provide approximately 8 μm resolution, which is suitable for bone growth quantification. Such μCT image-based approaches may be more suitable than histology-based approaches for quantifying bone growth as histology approaches reveal bone growth only in discrete slices that are typically positioned on a significantly courser grid than the 8 μm resolution of μCT slices.

In certain examples as shown herein, μCT imaging was performed on scaffold structures 100 on which bone 104 was grown. In particular, present examples of imaged bone growth on scaffold structures were obtained using scaffold structures implanted into small animals (e.g., mice) for six weeks, which were then removed and imaged. Turning to FIG. 1, in vivo imaging results are depicted for various scaffold structure topologies (i.e., trifurcating, clover, gyroid) and for a bovine bone Bio-Oss® control scaffold. In the depicted example, each scaffold structure 100 is depicted in a row, while the columns respectively correspond to imagery of the scaffold (leftmost), new bone (i.e., bone growth) 104 (rightmost), and scaffold+new bone (middle).

Based upon the imagery, it was determined that certain of the scaffold structures 100 showed comparable bone growth 104 to what was observed on Bio-Oss® control scaffold. It was also observed that bone growth 104 was surface topology dependent, with material and cavity surface topology both being factors that influenced the bone growth observed.

Figure 2:
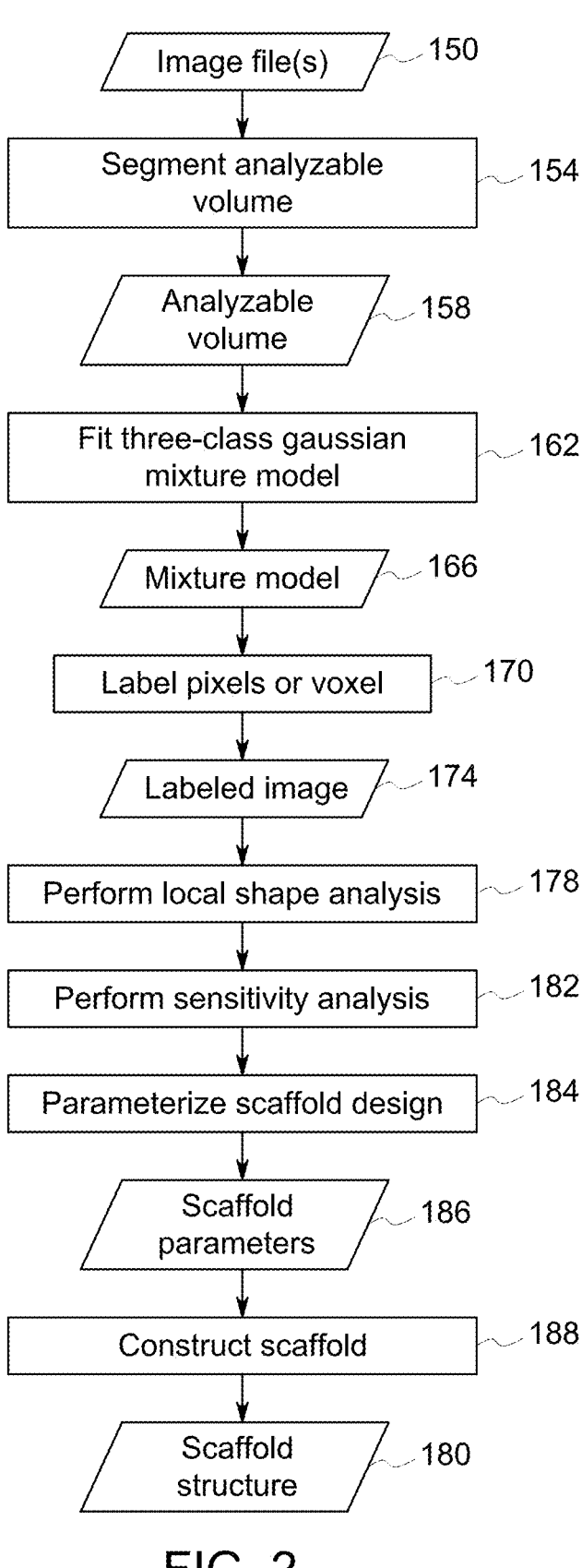
FIG. 2 depicts a process flow illustrating steps in the design and fabrication of a scaffold structure, in accordance with aspects of the present disclosure.

With the preceding in mind, FIG. 2 depicts aspects of a process for designing and fabricating a scaffold structure 100 optimized for facilitating bone growth and vascularization. In particular, FIG. 2, depicts steps in a process flow that relate to assessing bone growth from image data (e.g., μCT image data) for various scaffold structures and deriving scaffold parameters that may be used in fabricating an optimized or otherwise suitable scaffold structure 100.

In the depicted example, one or more images (e.g., DICOM images) of a scaffold structure 100 on which bone has been grown are acquired. The images 150 may be segmented (step 154) to obtain the analyzable volume 158. As used herein, the analyzable volume is the largest cuboidal region in the 3D image that does not enclose any region that is outside the scaffold. By way of example, in one embodiment the analyzable volume 158 may be obtained by finding the optimal foreground region as a minimal enclosing oriented bounding box, which is computationally intractable for the exact solution. Alternatively, a simplified approximated approach can be employed that estimates a convex-hull of the foreground region (e.g., pixels with large intensity) to obtain the analyzable volume.

Once the analyzable volume 158 has been obtained a three-class Gaussian mixture model 166 may be fitted (step 162) to the segmented region to classify (i.e., label) each pixel or voxel as one of three categories: background 200, scaffold 100, or bone 104 (and/or other tissue). A spatial prior (e.g., a spatial constraint to the segmented analyzable volume 158) may be employed as part of this process to improve robustness in the presence of noise. In addition, a label clean-up step may be performed to enforce prior knowledge of the imaged structure. By way of example, prior knowledge that the scaffold structure 100 is a contiguous structure and has a surface that is smooth may be leveraged in refining or updating the initially assigned labels. Similarly, the label clean-up step may be used to correct or update incorrect labels applied due to partial volume surface artifacts.

Figure 3:
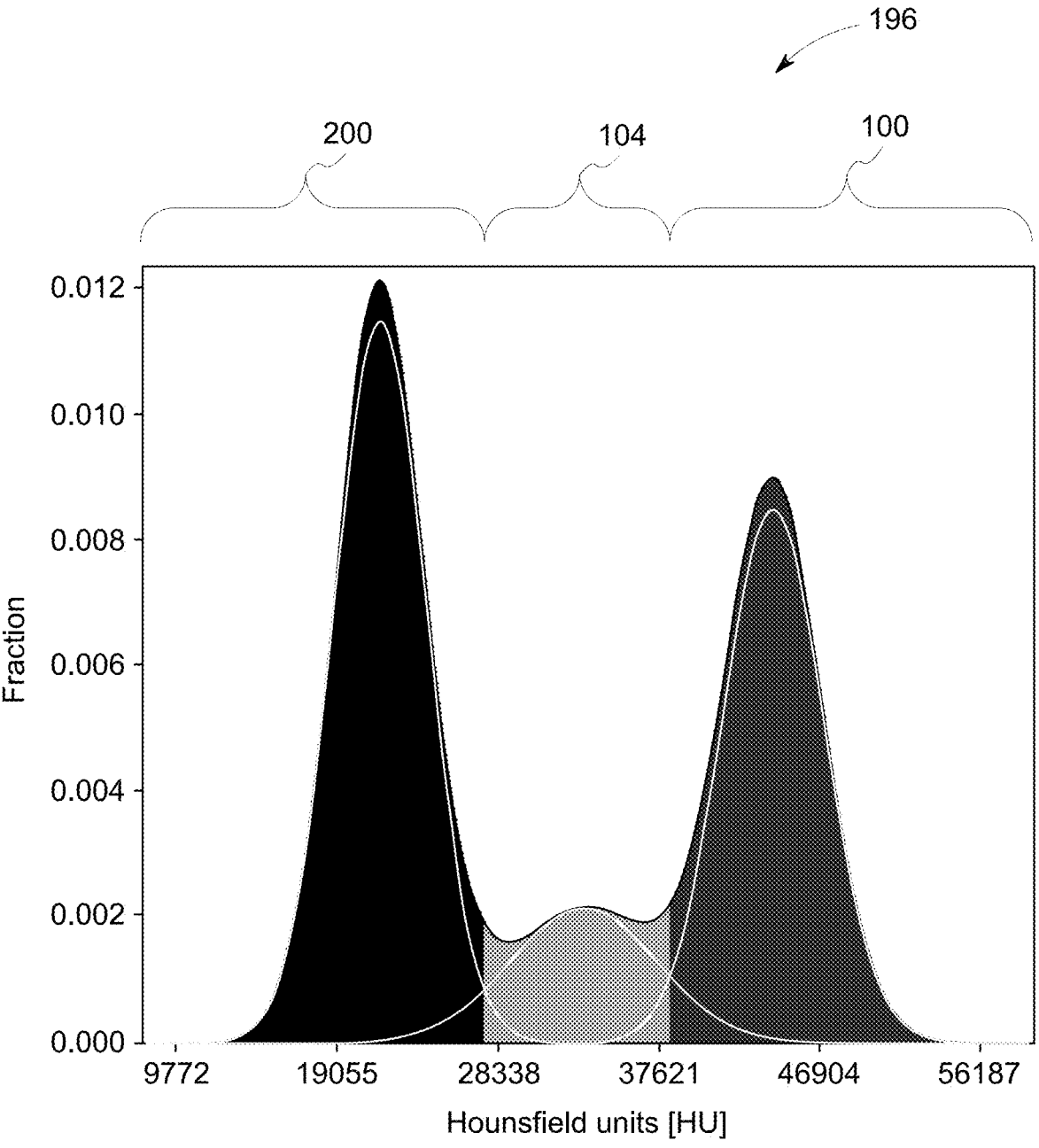
FIG. 3 depicts a three-class Gaussian mixture model, in accordance with aspects of the present disclosure.

In one implementation, the image data may be labeled (step 170) to create a labeled image(s) 174 based on the associated Hounsfield units assigned to a given voxel or pixel of the segmented analyzable volume 158. A visual representation of such a process is illustrated with respect to FIG. 3, in which image data corresponding to an analyzable volume 158 is fitted to a three-class Gaussian mixture model represented as a histogram 196 in which the X-axis corresponds to Hounsfield units. The Gaussian mixture model estimates the likelihood or probability of each image-pixel's membership to different classes based on its intensity and neighborhood, with the assumption that image data points are generated by mixture of three Gaussian distributions. The three estimated Gaussian distributions are shown as line plots on top of histogram 196. Each pixel is labeled as the class that has maximum likelihood estimates based on its intensity. This is shown as a three-shaded histogram 196, where each differential shading represents one of the class (background, scaffold, tissue/bone). In this example, cut-off points in Hounsfield units can be determined using the Gaussian likelihood estimates of the materials of interest and the ranges of Hounsfield units so identified can be used to label the pixels or voxels of the segmented region 158.

Figure 4:
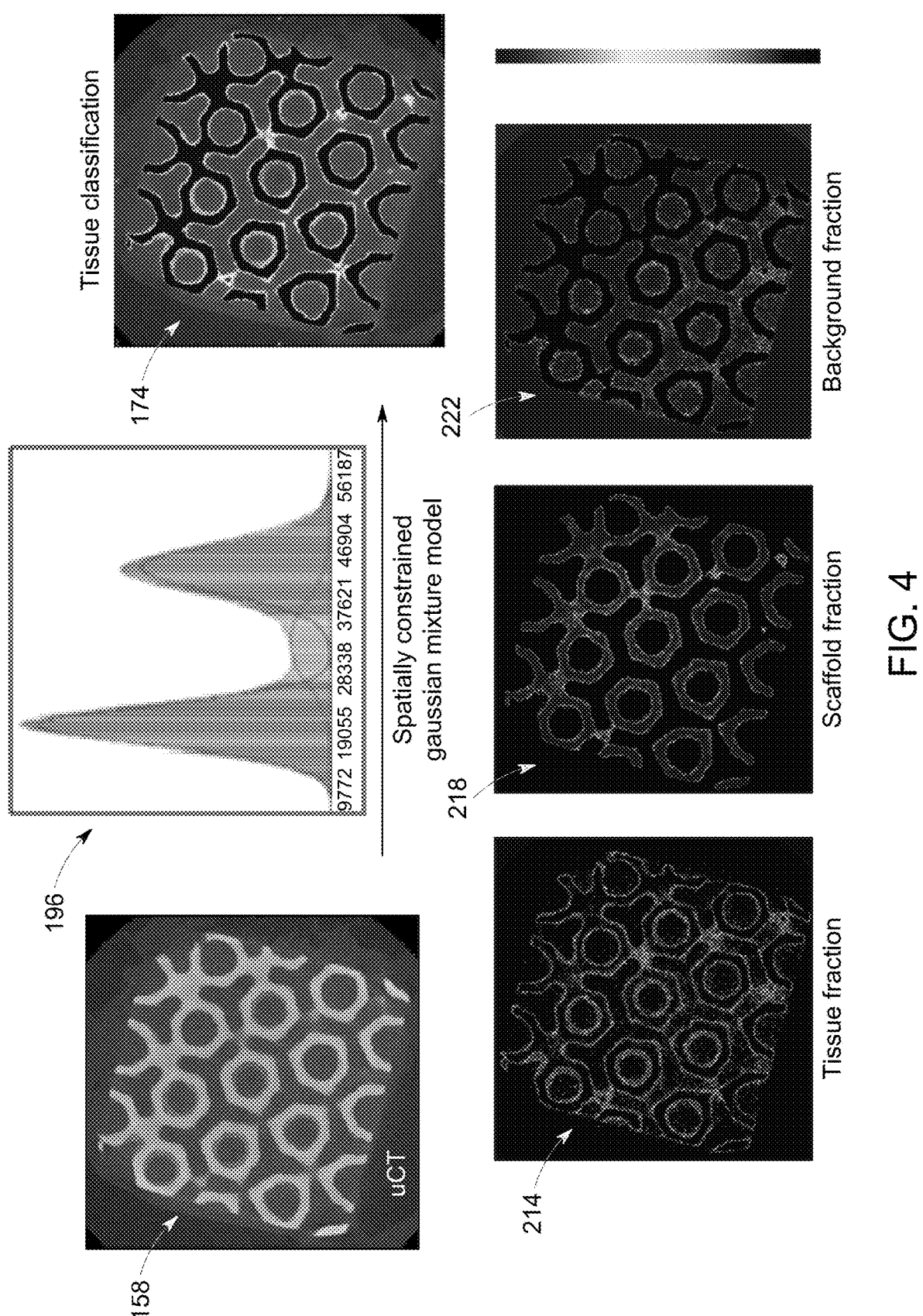
FIG. 4 depicts the use of the three-class Gaussian mixture model of FIG. 3 for classifying pixels or voxels, in accordance with aspects of the present disclosure.

This process is further illustrated in FIG. 4 in which an image sequence is visually represented of an analyzable volume 158 being fitted to a spatially constrained Gaussian mixture model, as represented by a histogram 196 of Hounsfeld units of pixels or voxels in the analyzable volume 158. Each pixel or voxel is labeled in accordance with the mixture model to generate a labeled image 174 (e.g., a tissue classified image). As shown in FIG. 4, based on the labeled pixels or voxels, representative images for each of the three classifications may also be generated (e.g., bone or tissue fraction image 214, a scaffold fraction image 218, and a background fraction image 222).

Turning back to FIG. 2, based on the labeled pixels or voxels, a local shape analysis may be performed (step 178). As part of the local shape analysis a smooth scaffold surface may be determined and each point of this surface can be characterized by a local topology and orientation. Local topology may be quantified at each point on the scaffold surface along with bone growth at that point, and the quantified relationship(s) between local topology and the local bone growth obtained. The quantified relationship(s) between local topology and local bone growth may be represented as a feature importance matrix, $\mathbb{F}$.

Unlike the global analysis discussed herein, which may broadly analyze bone growth in the context of global or overall characteristics of the scaffold structure 100 as a whole (such as material, unit-cell size, topology, and so forth), local shape analysis as discussed herein may relate to characteristics (e.g., local topology) of the individual or localized features of the repeatable pattern of open structures (e.g., cavities) comprising the scaffold structure 100, which may be characterized as repeated (periodic or otherwise) structures or features (e.g., cavity features) which together form the scaffold structure 100. Such local feature analysis may encompass curvature-based shape descriptors for one or more surface features, as well as Eigen and spherical harmonic-based cavity descriptors.

Figure 5:
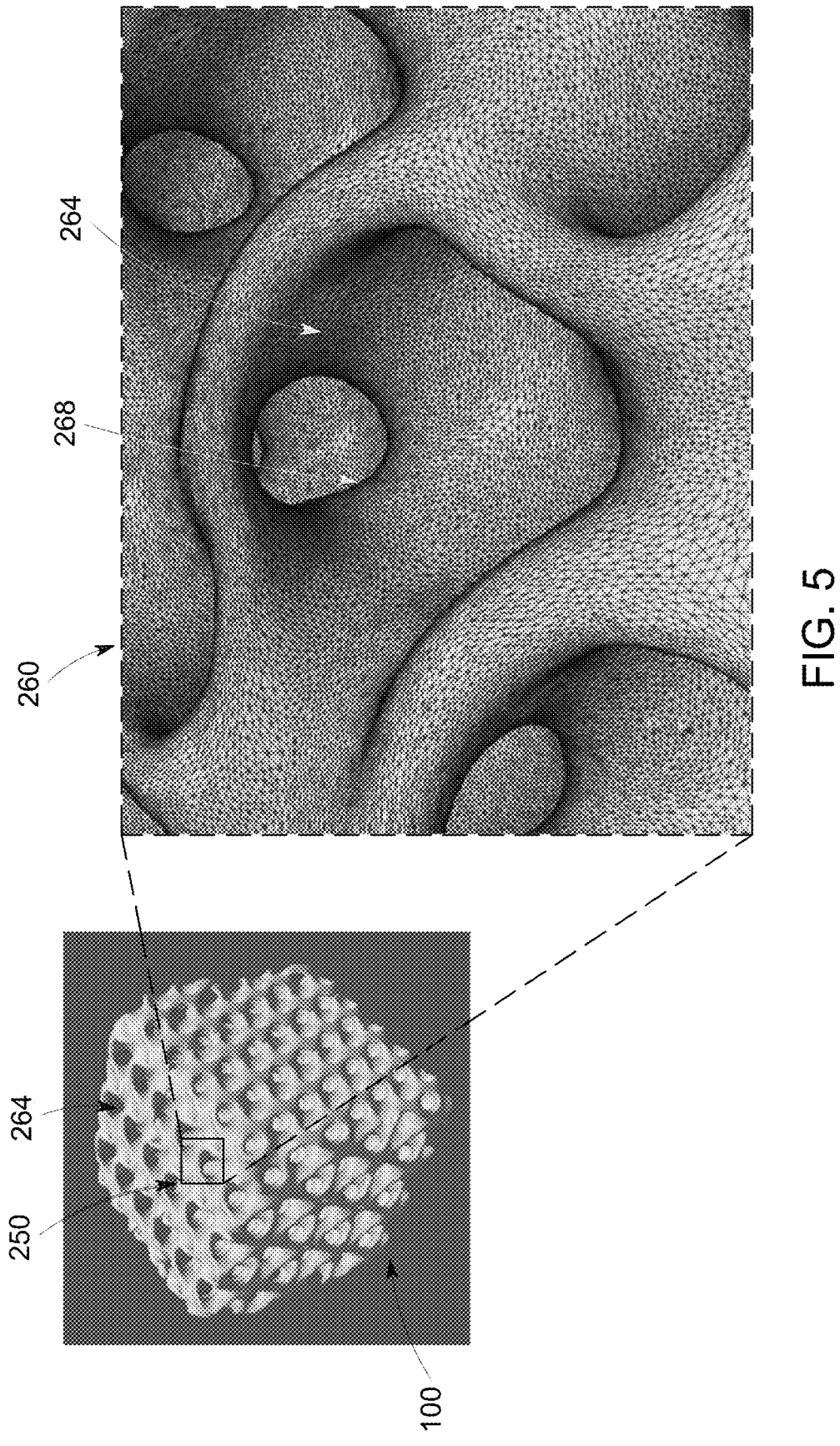
FIG. 5 depicts an example of a scaffold structure and an enlarged view of local pore features of the scaffold structure, in accordance with aspects of the present disclosure.

By way of example, FIG. 5 illustrates a view of a scaffold structure 100 comprised of repeating open structures (e.g., cavities) 264 on the left with an enlargement of a selected sub-region 250 depicted on the right showing a magnified view of the structures and features 268 defining the respective cavities. As discussed herein, cavity surface features 268 may be characterized in terms of continuous curves that are described using different formulations of the principal curvatures $k_1$ and $k_2$. As used herein a feature 268 may measure 10 μm to 1,000 μm. In the depicted example, each feature 268, and the surface in general may be represented or mapped as triangular sub-regions defined by respective vertices. As discussed herein, each local cavity feature 268 may be characterized by a number and placement of these vertices each with one or more curvature characteristic (e.g., shape index, Gaussian curvature, curvedness, and so forth). Local cavity features 268 may also be characterized by other characteristics including, but not limited to, unit cell size (i.e., the repeating unit), elongation, orientation, and/or other Eigen decomposition-based features. Characterization of such local features 268 may be useful in parameterizing, designing, and fabricating a scaffold structure 100 composed of repeating open structures (e.g., cavities) because cell growth (e.g., bone and vascular cell growth and differentiation) vary based on such features 268.

Correspondingly, characterizing and quantifying such local features 268 allows identification and optimization of those local shape attributes that affect bone growth. By way of example, and turning to Table 1, a breakdown of observed feature characteristics as they affect bone growth is provided. It may be appreciated that for each described features in the leftmost column of Table 1, the various other columns related to the respective feature may list multiple options for that field which may be read in combination with one another (e.g., for the Feature 0.65>s>0.25, each of the listed global topologies (e.g., Trifurcating, Gyroid 001, Gyroid 111) may be combined with each of the listed materials (e.g., HA and TCP) and/or combined with each of the listed cavity sizes (e.g., 350 μm and 500 μm)).

TABLE 1

| Features characteristics that encourage/discourage bone growth | | | | | |
|---|---|---|---|---|---|
| Shape Features | Feature unit | Bone Count | Topology | Material | Cavity Size |
| 0.84 > s > −0.45 | Unitless | Moderate, High | | All | |
| s < −0.45 | Unitless | Almost none | | All | |
| 0.65 > s > 0.25 | Unitless | High | Trifucating Gyroid 001 Gyroid 111 Clover | HA TCP | 350 μm 400 μm 500 μm |
| 30 > R > 15 | 1/mm | Almost None | | All | |
| R ≈ 5 ± 1 | 1/mm | High | | All | |
| 13.5 > R > 1.4 | 1/mm | High, Moderate | | All | |
| 5 > R > 0.5 | 1/mm | High, Moderate | | Bio-Oss ® | |
| −60 < GC < 20 | 1/mm² | High, Moderate | | All | |
| −80 < GC < 0 | 1/mm² | High | | Bio-Oss ® | |
| GC > 20 | 1/mm² | Almost None | | All | |
| MC < −7.5 Or MC > 5 | 1/mm | Almost None | | All | |
| −7.5 < MC < 5 | 1/mm | High, Moderate | | All | |

In terms of further clarification from observed results, greater bone growth was observed for HA relative to TCP in terms of material effects. In terms of global topology gyroid 001 exhibited the greatest degree of bone growth, followed by gyroid 111, followed by trifurcating and clover, which were substantially equal. In terms of cavity size, 500 μm exhibited the greatest degree of bone growth, followed by 350 μm and 400 μm, which were substantially equal. With this in mind, in practice a scaffold structure 100 as presently described may comprise a propensity of points (e.g., 2.5% or more points of the respective surface) having a shape index between −0.45 and 0.84. Similarly, in practice a scaffold structure 100 as presently described may comprise a propensity of points (e.g., 2.5% or more points of the respective surface) having a curvedness between 1.4 and 13.5. Further, a scaffold structure 100 as presently described may comprise unit cell sizes (i.e., repeating units) in the range of greater than 100 microns and less than 2,000 microns, such as greater than 300 microns and less than 1,000 microns. Similarly, in other embodiments, a scaffold structure 100 may comprise a propensity of points (e.g., 2.5% or more points of the respective surface) having a mean curvature between −7.5 and 5. Similarly, in practice a scaffold structure 100 as presently described may comprise a propensity of points (e.g., 2.5% or more points of the respective surface) having a Gauss curvature between −60 and 20.

Figure 6:
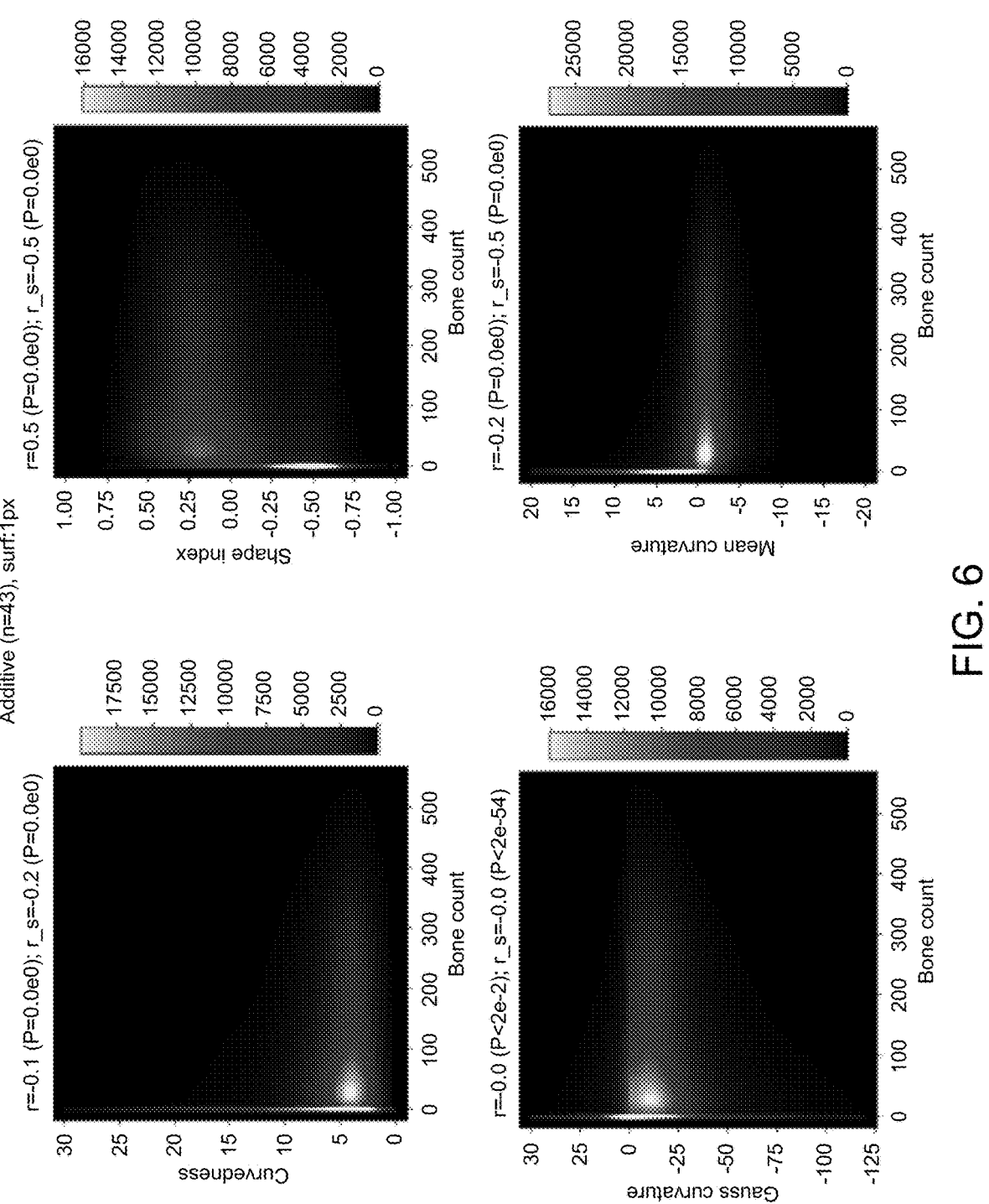
FIG. 6 illustrates a series of heatmaps generated for additively manufactured scaffold samples and having bone count along the x-axis and, from left to right, curvedness, shape index, Gauss curvature, and mean curvature along the y-axis.
Figure 7:
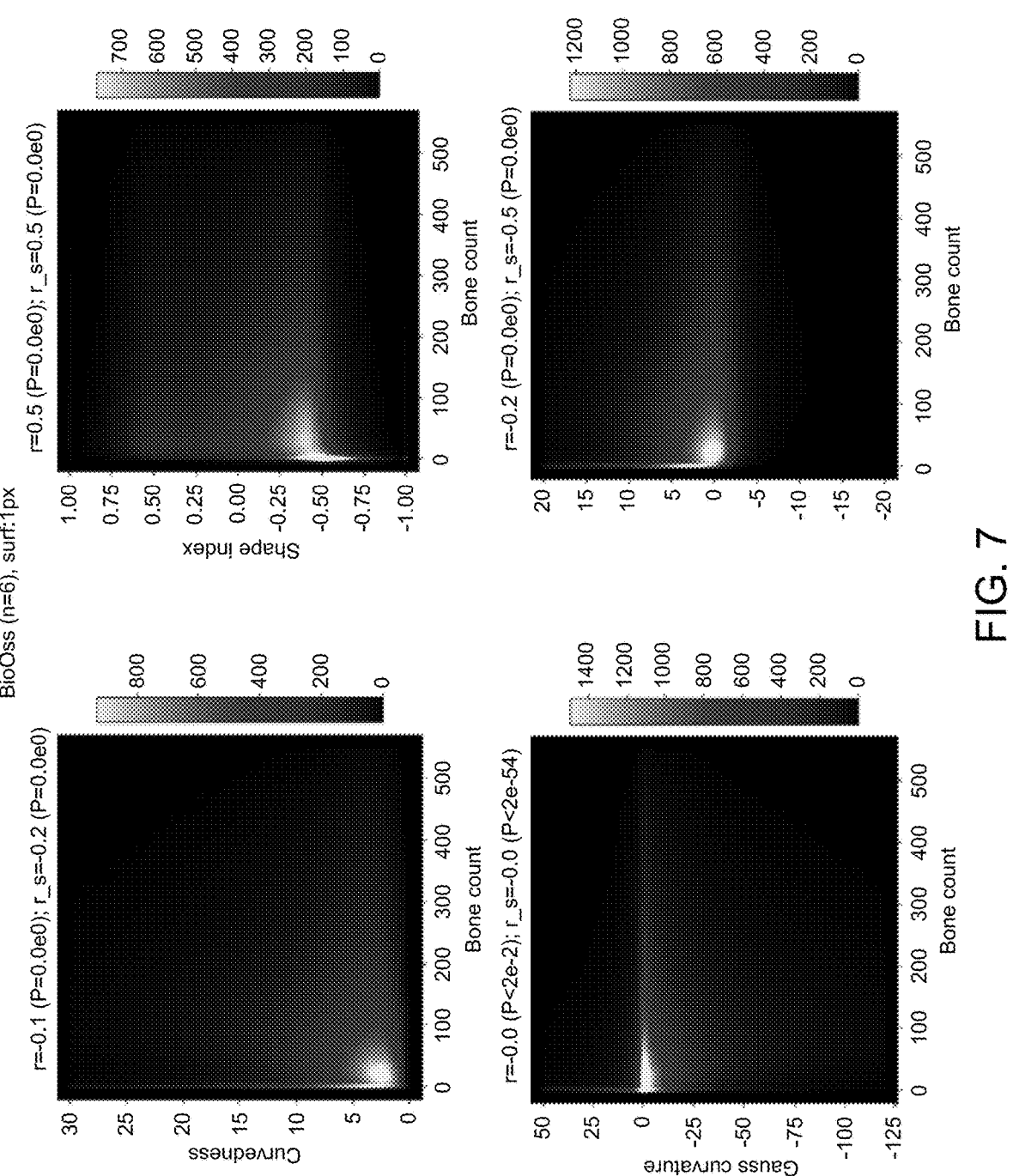
FIG. 7 illustrates a series of heatmaps generated for control samples and having bone count along the x-axis and, from left to right, curvedness, shape index, Gauss curvature, and mean curvature along the y-axis.

By way of further illustration, FIGS. 6 and 7 illustrate heat maps comprising plots in two-dimensions and illustrating bone growth in two-dimensions. Each of FIGS. 6 and 7 comprise a series of four heat map depictions each corresponding to a different local topology parameter for a given sample set. In particular, each series of heatmaps illustrate bone count along the x-axis and, from left to right, illustrate curvedness, shape index, Gauss curvature, and mean curvature along the y-axis. FIG. 6 illustrates heat maps for these parameters for additively manufactured scaffold samples of all global topologies and FIG. 7 illustrates heat maps for these parameters for Bio-Oss® control samples.

Figure 8:
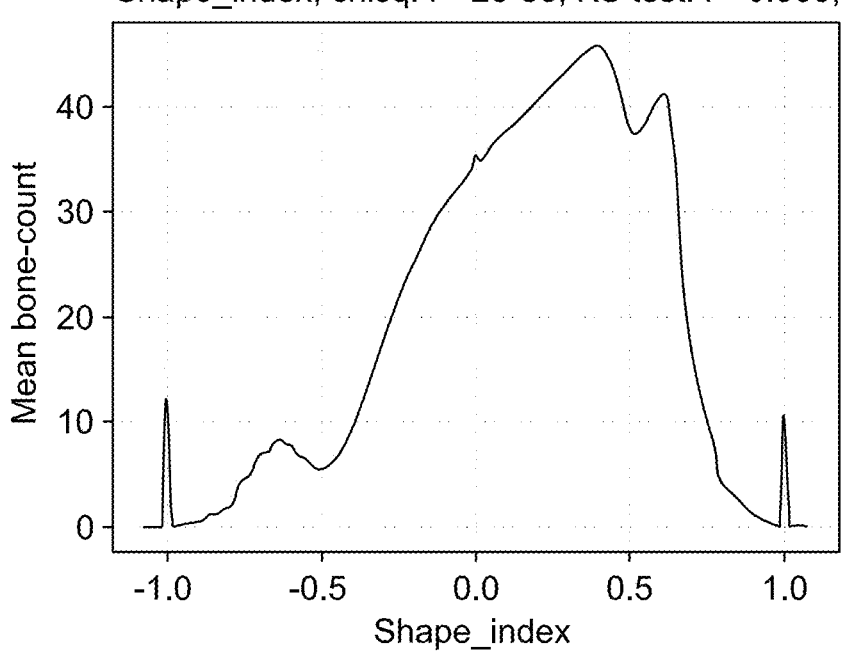
FIG. 8 illustrates the relationship between shape index (x-axis) and mean bone count (y-axis)
Figure 9:
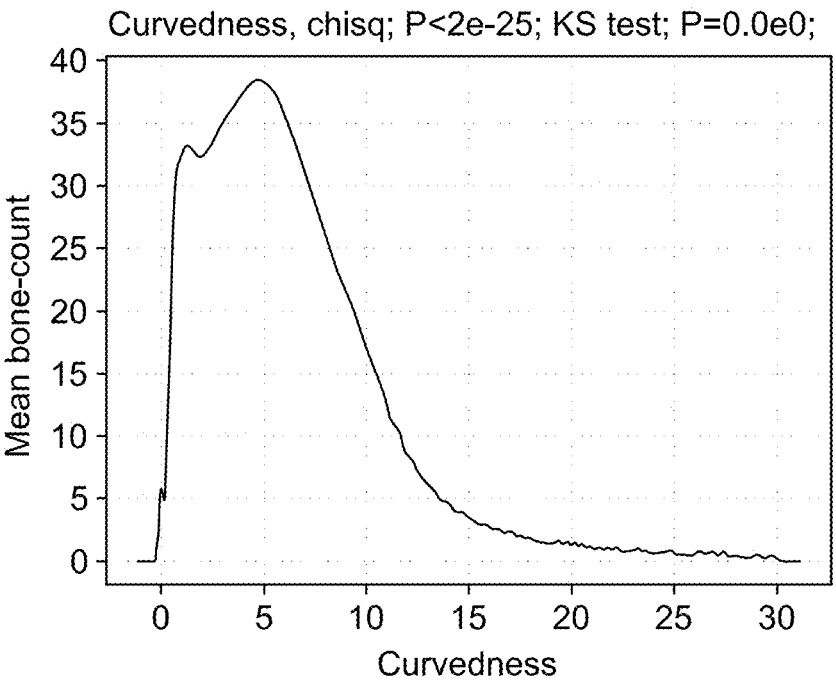
FIG. 9 illustrates the relationship between curvedness (x-axis) and mean bone count (y-axis)
Figure 10:
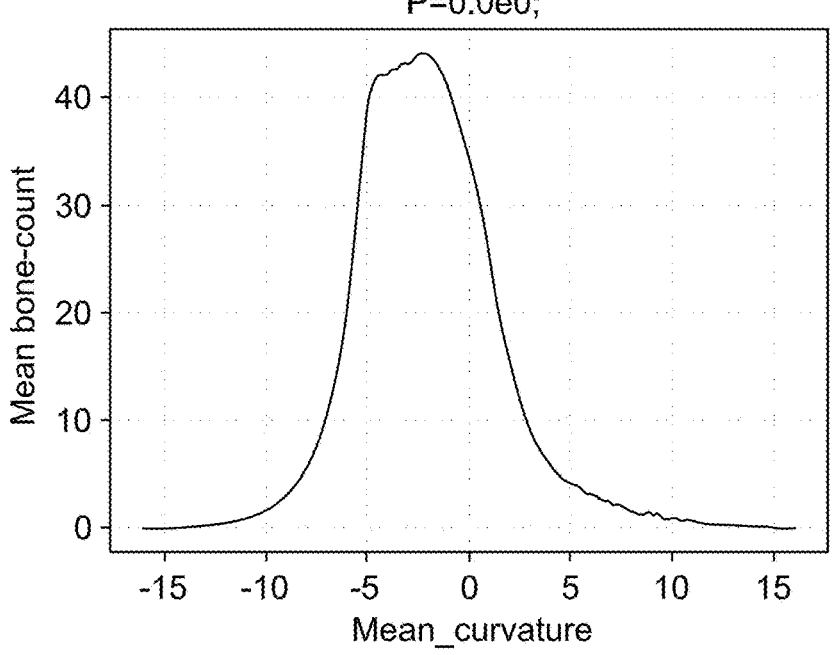
FIG. 10 illustrates the relationship between mean curvature (x-axis) and mean bone count (y-axis)
Figure 11:
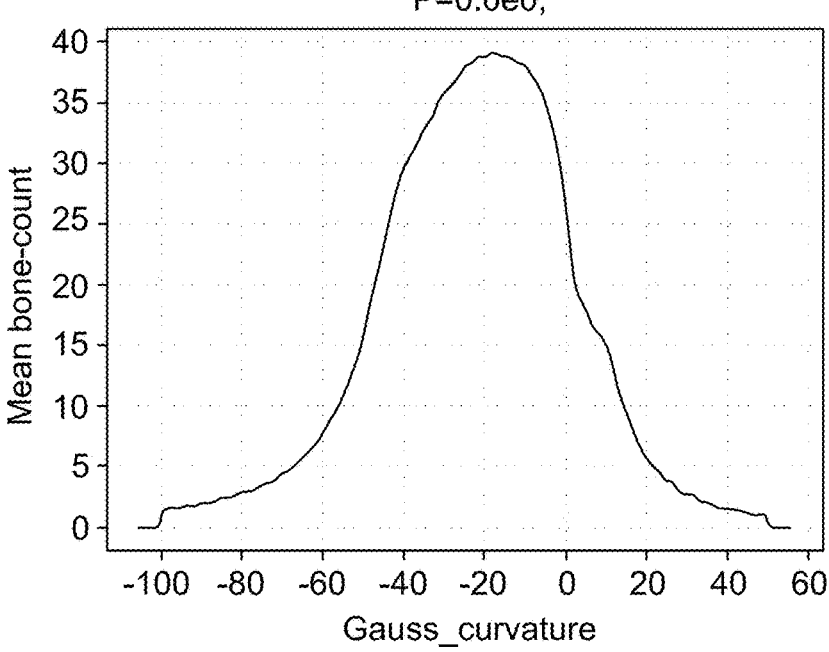
FIG. 11 illustrates the relationship between Gauss curvature (x-axis) and mean bone count (y-axis)

While the heat maps of FIGS. 6-7 provide one illustration of the interrelationships between various local topology parameters and bone growth, FIGS. 8-11 illustrate the relationship between bone growth and various local topology parameters. By way of example, FIG. 8 illustrates the relationship between shape index (x-axis) and mean bone count (y-axis), FIG. 9 illustrates the relationship between curvedness (x-axis) and mean bone count (y-axis), FIG. 10 illustrates the relationship between mean curvature (x-axis) and mean bone count (y-axis), and FIG. 11 illustrates the relationship between Gauss curvature (x-axis) and mean bone count (y-axis). As may be appreciated, in making design decisions parameterizing local topology for a bone growth substrate, the local topology may be designed so as take advantage of one such parameter (e.g., shape index, curvature, mean curvature, or Gauss curvature), two such parameters (e.g., shape index in conjunction with curvature in one example or mean curvature in conjunction with Gauss curvature in another example), three such parameters, and so forth.

Figure 12:
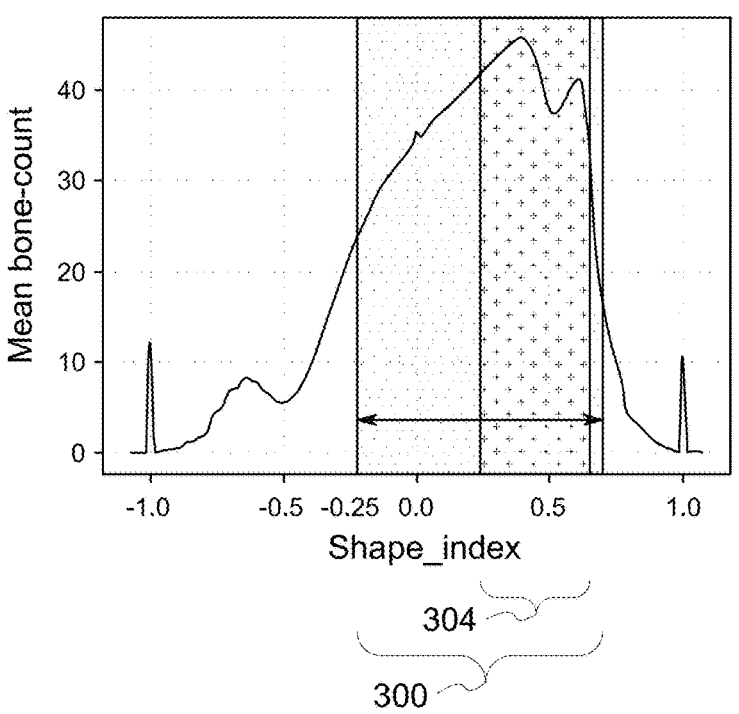
FIG. 12 depicts the plot of FIG. 8 further illustrating sub-ranges corresponding to improved bone growth.
Figure 13:
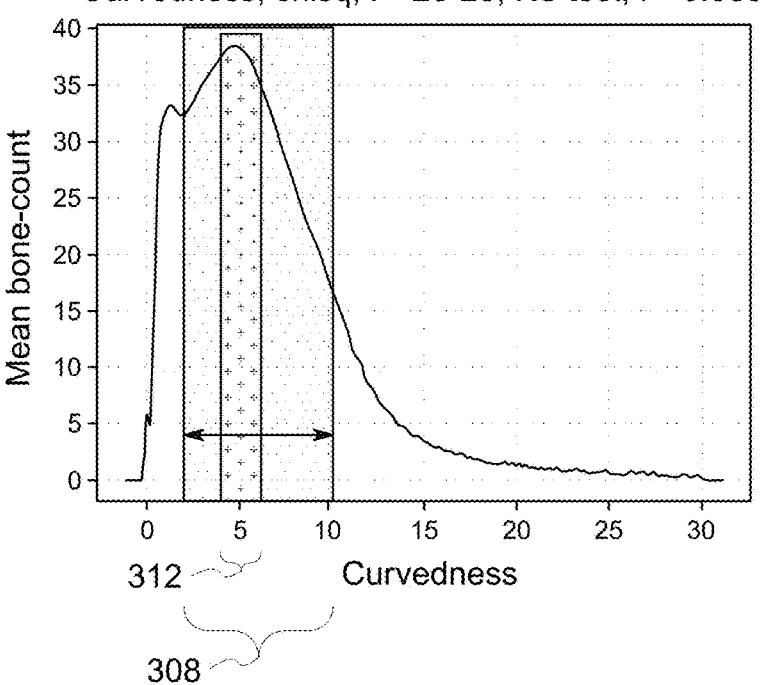
FIG. 13 depicts the plot of FIG. 9 further illustrating sub-ranges corresponding to improved bone growth.

By way of further example, the graphs of two of these parameters are replicated in FIGS. 12 and 13 with overlaid shading to indicate nested sub-ranges from which parameter values may be drawn from. For example, FIG. 12 illustrate the plot of mean bone count (y-axis) versus shape index (x-axis) with a range 300 and a sub-range 304 illustrated from which shape index values may be selected so as to optimize bone growth. FIG. 13 illustrates a similar range 308 and sub-range 312 with respect to curvedness.

Figure 14:
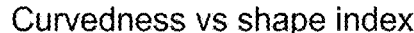
FIG. 14 depicts a heat map of curvedness versus shape with nested sub-regions corresponding to improved bone growth.
Figure 14:
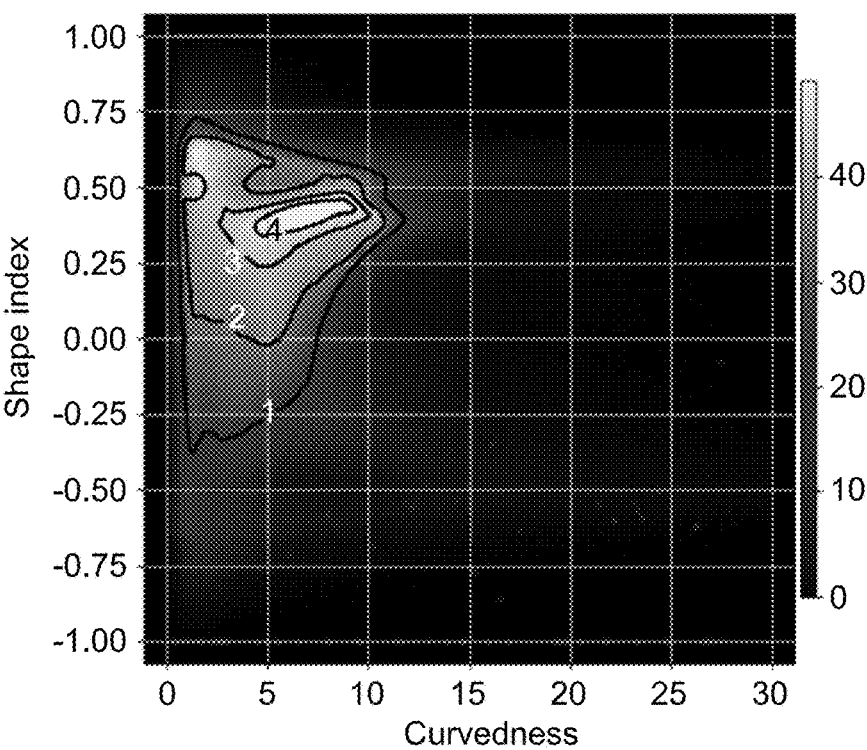
Figure 15:
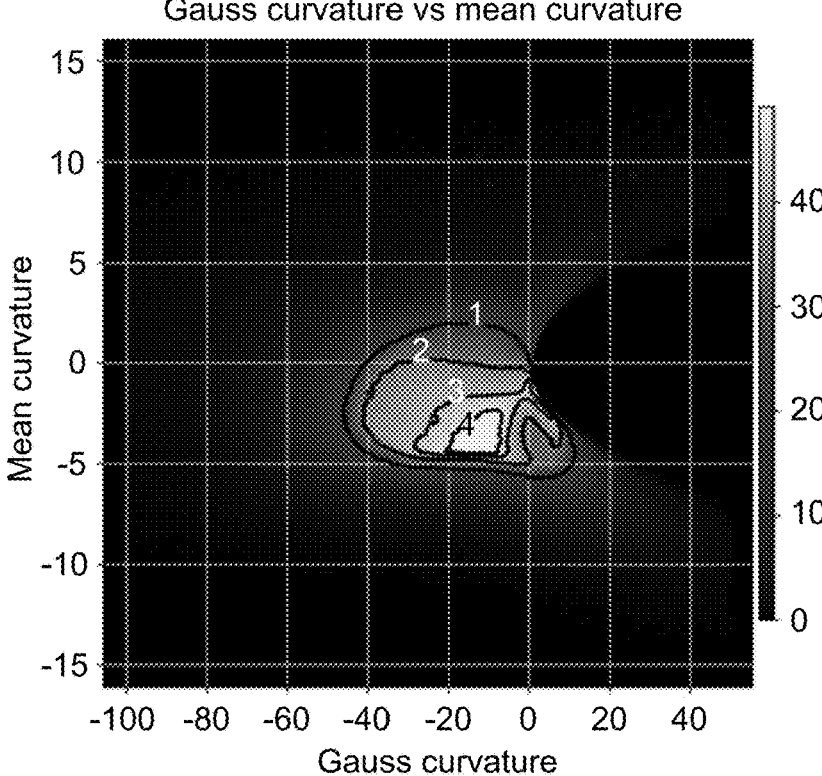
FIG. 15 depicts a heat map of mean curvature versus Gauss curvature with nested sub-regions corresponding to improved bone growth.

As may be appreciated, in certain implementations where local topology is optimized using two or more local topology parameters, the optimal combination or region of parameters for bone growth may not be easily or simply characterized by two ranges of values. By way of example, and turning to FIGS. 14 and 15, two heat maps are illustrated along with a region and nested sub-region of suitable local topology parameters. Turning to FIG. 14, bone growth is illustrated in a heat map and plotted against shape index (y-axis) and curvedness (x-axis). Region 1 and sub-region 2, 3, and 4 illustrate suitable regions having parameters tuned for bone growth. Similarly, in FIG. bone growth is illustrated in a heat map and plotted against mean curvature (y-axis) and Gauss curvature (x-axis). Region 1 and sub-region 2, 3, and 4 illustrate suitable regions having parameters tuned for bone growth.

With the preceding in mind, and in the context of configuring or designing a scaffold for facilitating bone growth, in certain implementations as discussed herein the scaffold solid volume may be configured or designed so as to include a plurality of repeating structures each defined by a set of local topologies. These local topologies may be characterized by a subset of points in their respective surface having one or more of a shape index, a curvedness, a mean curvature, a Gauss curvature, or other topology parameter with a range of values corresponding to improved bone growth. In certain implementations, the subset of point may comprise 2.5%, 5%, 10%, 20%, 30%, or 40% of the points of the respective surface.

Turning back to FIG. 2, a sensitivity analysis may be performed (step 182). In one implementation this may be a global topology and/or material analysis of bone growth based on the labeled image 174. By way of example, global bone growth distribution may be analyzed in accordance with the formula:

$$\text{Bone Volume } \% = 100 \times \frac{\text{Bone Volume}}{\text{Total Volume of the Open Space Structure}} \quad (3)$$

Figure 16:
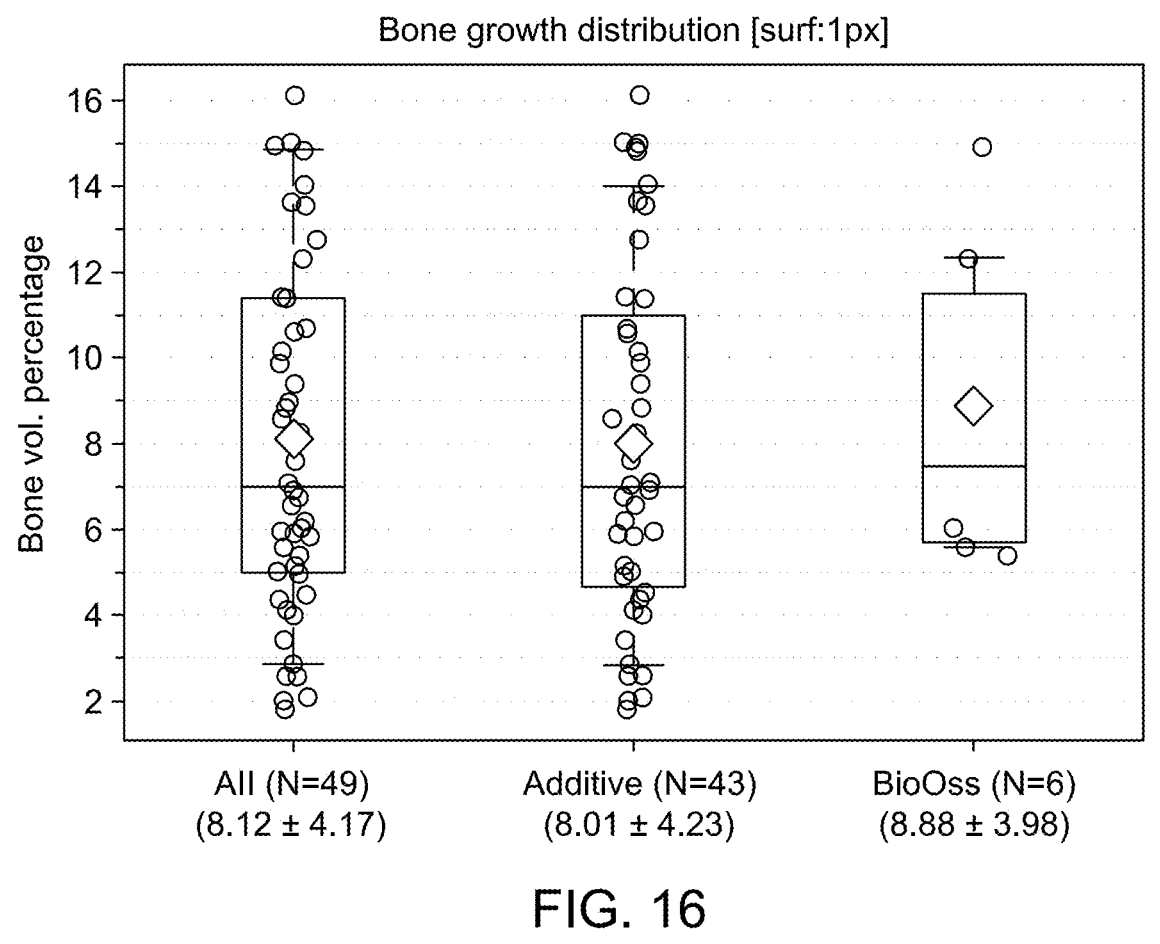

In one such analysis, to eliminate the effect of partial volume effects in the μCT imaging voxels initially classified and labelled as a bone or tissue voxel that is within 1, 2, or 3 voxels of a voxel initially classified and labelled as a scaffold voxel can be eliminated from voxels counted in the bone volume. Results of one such analysis are shown graphically in FIG. 16, which illustrates box plots of bone volume percentage for additively manufactured scaffolds 100 (middle), Bio-Oss® controls (right), and the combined results (left) with 1 voxel eliminated using this method. As demonstrated by these results, the additive scaffolds and controls show similar bone growth, with wider variation associated with the additively manufactured scaffolds.

Figure 17:
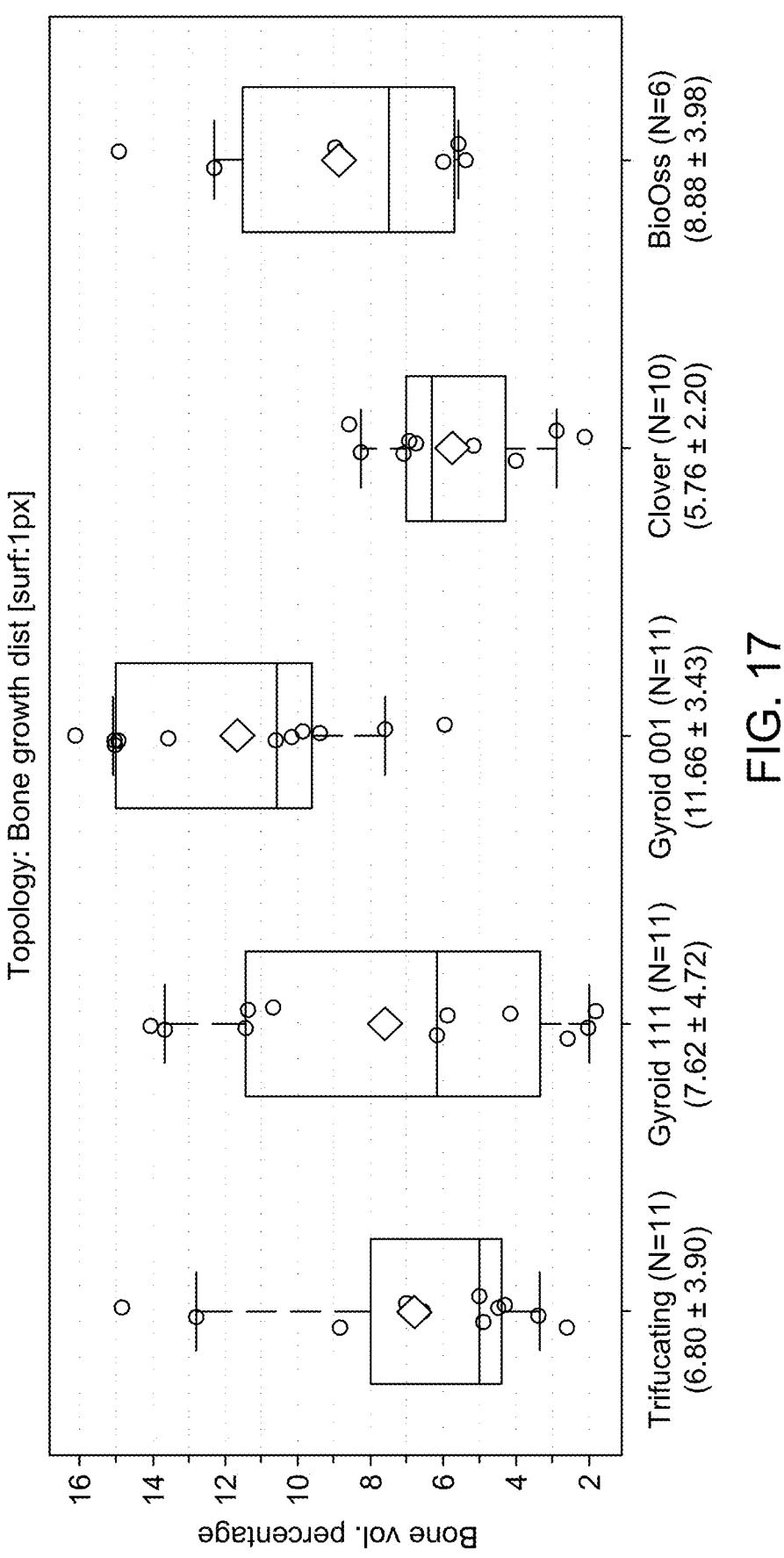
FIG. 17 depicts box plots of bone volume percentage for different topologies of scaffold structures and a control.
Figure 18:
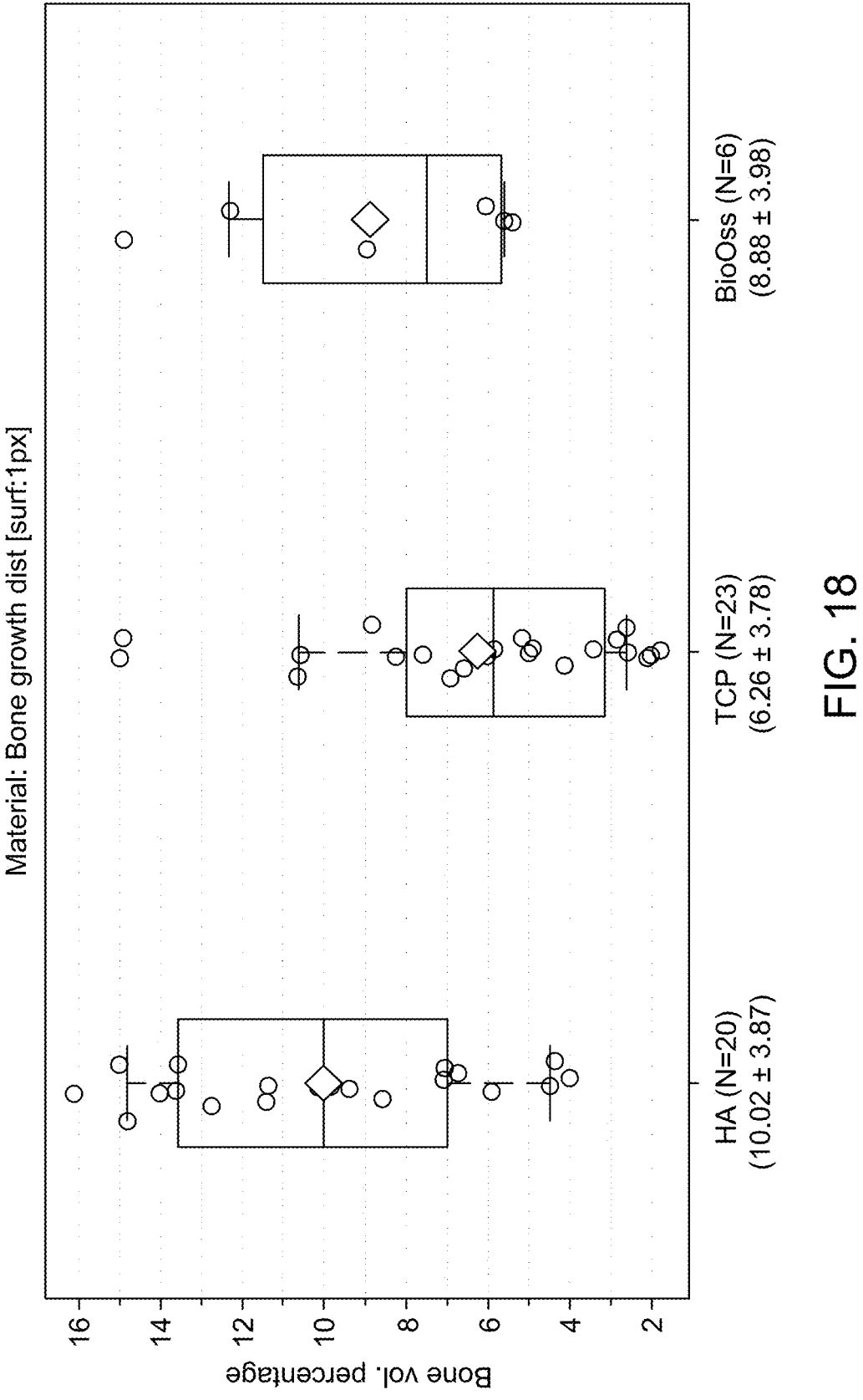
FIG. 18 depicts box plots of bone volume percentage for different material compositions of scaffold structures and a control.
Figure 19:
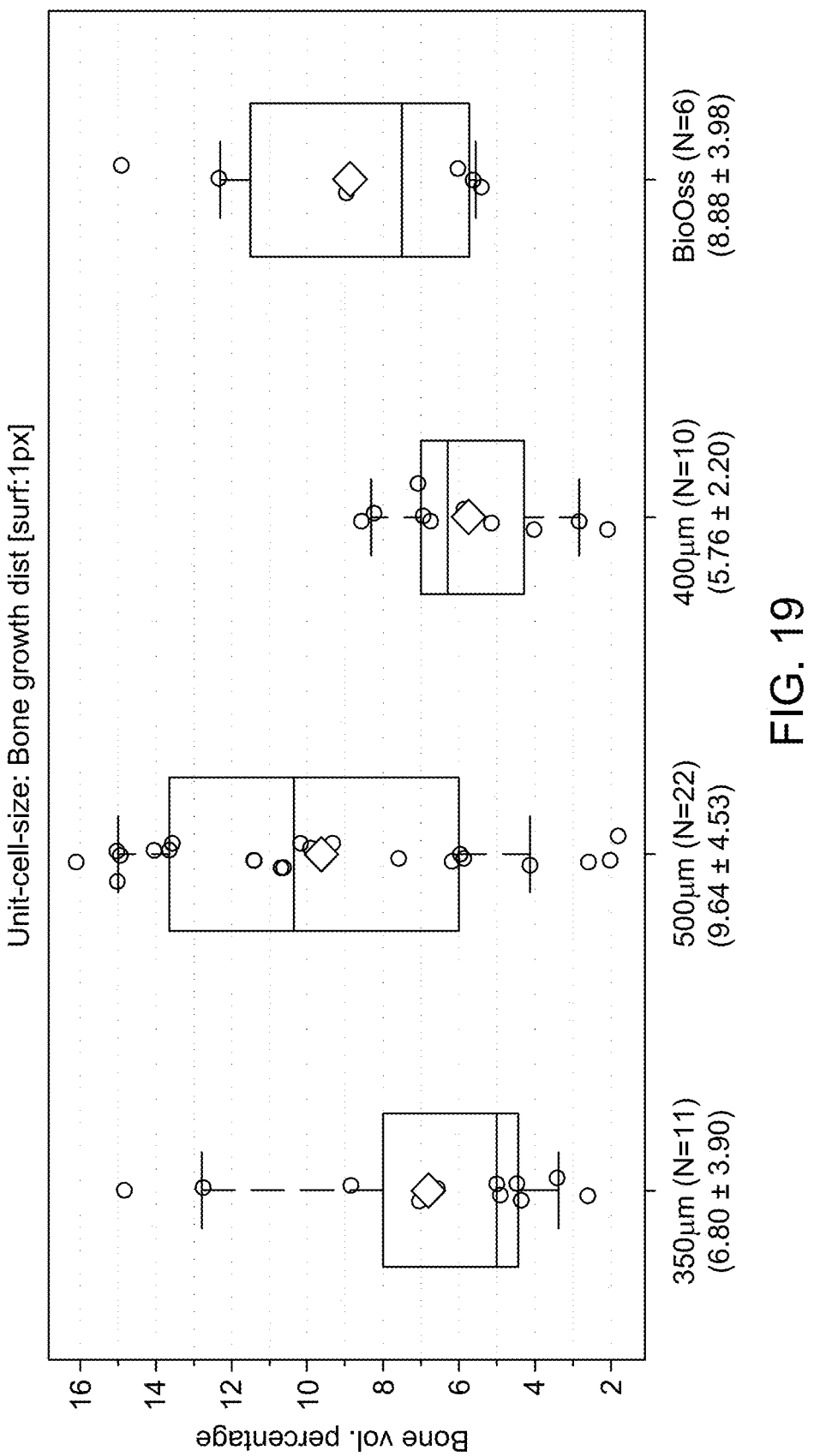
FIG. 19 depicts box plots of bone volume percentage for different unit-cell sizes associated with scaffold structures and a control.

In terms of factors that may impact global bone growth, further box plots provided in FIGS. 17-19 illustrate how bone volume percentage was observed to vary based on global topology (FIG. 17), material (FIG. 18), and unit-cell size as defined as the length of the repeating unit of the scaffold geometry (FIG. 19) as set forth in Table 2. For example, FIG. 17 illustrates respective box plots for the Bio-Oss® control along with trifurcating, gyroid 111, gyroid 001, and clover global topologies. As shown, observed bone volume percentage varied based on global topology. Similarly, FIG. 18 illustrates respective box plots for the Bio-Oss® control along with scaffold structures formed using hydroxyapatite (HA) and tricalcium phosphate (TCP) ceramics. As shown, observed bone volume percentage also varied based on material composition of the scaffold structure 100. Lastly, turning to FIG. 19, respective box plots are shown for the Bio-Oss® control along with scaffold structures having unit-cell sizes (e.g., feature sizes) of 350 μm, 400 μm, and 500 μm. As shown, observed bone volume percentage also varied based on unit-cell size of the scaffold structure 100. As may be appreciated from these figures, bone growth appears to depend on topological features and feature size as well as material composition of the scaffold structures 100.

Turning back to FIG. 2, the various parameters and matrices derived from analysis of scaffold structures having different topologies, compositions, and local features may be used to identify and parameterize (step 184) a scaffold design. By way of example, scaffold structure parameters 186 for promoting or improving bone growth may be determined by maximizing or optimizing one or more components of:

$$\hat{t} = \underset{\bar{t}}{\mathrm{argmin}} \| \mathfrak{F}(\mathcal{O}(\bar{t})) - \mathbb{F} \|^2 \tag{4}$$

where $\mathfrak{F}$ is a feature operator, $\mathcal{O}$ is a triply periodic minimal surface (TPMS) operator, $\bar{t}$ is a TPMS parameter, and $\mathbb{F}$ is the feature importance matrix. The parameters 186 so identified and optimized may be used to construct (step 188) a scaffold structure 100, such as via an additive manufacturing process (e.g., 3D-printing). While this example is given for a global topology that can be described with respect to parameters for a triply periodic minimal surface it will be recognized by those skilled in the art that maximizing the number of local topologies that maximize bone growth is not limited to TPMS structures.

With respect to the construction of the scaffold structures 100, in certain implementations lithography based additive manufacturing techniques, such as digital light processing (DLP) techniques, which are suitable for fabricating complex geometries using polymers, metals, and/or ceramics, may be employed. By way of example, a DLP process may be used to fabricate biocompatible ceramic scaffold structures 100 that support osteogenesis and provide a degree of load-bearing capacity, such as may be suitable for a spinal implant.

In one example of an implementation, a slurry consisting of hydroxyapatite dispersed in a photocurable resin was employed in conjunction with a DLP printing system where the build plate was above a vat holding the ceramic slurry. During the build process, the build plate was lowered into the ceramic slurry and a light image was projected from below the vat, curing the layer. The build plate was lifted with the cured layer, the vat rotated to recoat with fresh slurry, and then the build plate was lowered into the slurry to cure the next slice. Nominal dimensions of scaffolds were 5 mm tall, 5 mm wide, and 5 mm deep. The scaffolds were printed with a 1.13 isotropic scale factor applied to account for firing shrinkage. Print layer thickness of 25 microns was used and the cure time per layer was 3.5 seconds at full LED intensity. The printed parts were removed from the build plate and cleaned to remove excess slurry from the interior of the scaffold. After cleaning, scaffolds were fired in two steps. The first step was a low temperature firing to 205° C. to remove volatile organic components prior to debinding and sintering. The second step was a high temperature firing to sinter the parts to 1300° C. Scaffold structures produced in this manner were observed to have mechanical strength comparable or equivalent to human trabecular bone, and thus provide load-bearing functionality.

Technical effects of the preceding include, but are not limited to a bone defect repair system that includes a scalable fabrication system which can support the development of fully resorbable, biocompatible scaffolds. Modeling of scaffold architecture may be optimized to meet the specific needs for spinal implants or other bone defect repairs. Custom design of scaffold structures for patients with spinal trauma injuries may provide improved patient outcomes and facilitate vascularization, bone formation and neural ingrowth, and subsequent resorption of the scaffold.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An implantable bone scaffold structure for facilitating bone growth, comprising:
   a scaffold volume comprising a plurality of repeating structures defined by surface area and local topology, wherein at least 2.5% of the surface area comprises local topologies with a shape index between −0.45 and 0.84 and a curvedness between 1.4 and 13.5.

2. The bone scaffold structure of claim 1, wherein at least 5.0% of the surface area comprises local topologies with a shape index between −0.45 and 0.84 and a curvedness between 1.4 and 13.5.

3. The bone scaffold structure of claim 1, wherein at least 10.0% of the surface area comprises local topologies with a shape index between −0.45 and 0.84 and a curvedness between 1.4 and 13.5.

4. The bone scaffold structure of claim 1, wherein at least 20% of the surface area comprises local topologies with a shape index between −0.45 and 0.84 and a curvedness between 1.4 and 13.5.

5. The bone scaffold structure of claim 1, wherein the local topologies are characterized by a subset of points in their respective surface having a shape index between 0.25 and 0.65.

6. The bone scaffold structure of claim 1, wherein the local topologies are characterized by a subset of points in their respective surface having a curvedness between 2 and 10.

7. The bone scaffold structure of claim 1, wherein the scaffold structure comprises a sintered ceramic body.

8. The bone scaffold structure of claim 1, wherein the scaffold structure comprises a biologically compatible ceramic material.

9. The bone scaffold structure of claim 8, wherein the biologically compatible ceramic material comprises one or more of materials in the calcium phosphate (CaP) class of materials, hydroxyapatite (HA) ceramic, tricalcium phosphate (TCP), calcium sulfates, CaP cements, biphasic CaP, beta TCP, silicon nitride, aluminum oxide, zirconium oxide, bioactive glasses, or carbon-silicon.

10. The bone scaffold structure of claim 1, wherein the scaffold structure comprises a biologically compatible polymeric material.

11. The bone scaffold structure of claim 10, wherein the biologically compatible polymeric material comprises one or more of polycaprolactone (PCL), polyether ether ketone (PEEK), poly(methyl methacrylate) (PMMA), polylactic acid (PLA), polytetrafluoroethylene, or polyurethane.

12. The bone scaffold structure of claim 1, wherein the scaffold structure comprises a biologically compatible metal or metal alloy.

13. The bone scaffold structure of claim 12, wherein the biologically compatible metal or metal alloy comprises one or more of titanium or titanium alloys, cobalt chrome, or stainless steel.

14. The bone scaffold structure of claim 1, wherein the plurality of repeating structures comprise repeating units having unit cell sizes between 100 μm to 2,000 μm.

15. The bone scaffold structure of claim 1, wherein the plurality of repeating structures comprise repeating units having unit cell sizes between 300 μm to 1,000 μm.

\* \* \* \* \*